US010792433B2

(12) United States Patent
Rolfe et al.

(10) Patent No.: US 10,792,433 B2
(45) Date of Patent: Oct. 6, 2020

(54) SYRINGE ASSEMBLY

(71) Applicant: IPSEN PHARMA, Boulogne Billancourt (FR)

(72) Inventors: Steven Mark Guy Rolfe, New Barnet (GB); Andrew Lewis, West Bridgford (GB)

(73) Assignee: IPSEN PHARMA, Boulogne Billancourt (FR)

( * ) Notice: Subject to any disclaimer, the term of this patent is extended or adjusted under 35 U.S.C. 154(b) by 88 days.

(21) Appl. No.: 15/739,551

(22) PCT Filed: Jul. 1, 2016

(86) PCT No.: PCT/EP2016/065584
§ 371 (c)(1),
(2) Date: Dec. 22, 2017

(87) PCT Pub. No.: WO2017/001682
PCT Pub. Date: Jan. 5, 2017

(65) Prior Publication Data
US 2018/0169343 A1    Jun. 21, 2018

(30) Foreign Application Priority Data
Jul. 1, 2015   (EP) .................................... 15306064

(51) Int. Cl.
*A61M 5/315* (2006.01)
*A61M 5/31* (2006.01)

(52) U.S. Cl.
CPC ...... *A61M 5/31501* (2013.01); *A61M 5/3148* (2013.01); *A61M 2005/31508* (2013.01); *A61M 2209/06* (2013.01)

(58) Field of Classification Search
CPC .... A61M 5/31501; A61M 2005/31508; A61M 2209/06
See application file for complete search history.

(56) References Cited

U.S. PATENT DOCUMENTS 6,030,363 A * 2/2000 Kriesel ............... A61M 5/1454
604/132
2011/0196313 A1   8/2011 Mudd
(Continued)

FOREIGN PATENT DOCUMENTS

FR          2347056 A1    11/1977
WO      2005084734 A1     9/2005

OTHER PUBLICATIONS

International Search Report dated Sep. 2, 2016 during the prosecution of International Application No. PCT/EP2016/065584.

*Primary Examiner* — Lauren P Farrar
(74) *Attorney, Agent, or Firm* — Troutman Pepper Hamilton Sanders LLP (57) ABSTRACT

The present invention concerns a syringe assembly comprising a hollow tubular syringe body, having a proximal end and a distal end, a plunger rod, axially movable in the syringe body between an initial position and a final position. The assembly also includes a support transversally stiff for supporting the plunger rod, the support having a distal end and a proximal end respectively transversally fixed to the syringe body and to the plunger rod, the proximal end of the support being movable with respect to the syringe body.

9 Claims, 8 Drawing Sheets (56) References Cited

U.S. PATENT DOCUMENTS

2013/0085457 A1* 4/2013 Schiff ................ A61M 5/31511
                                                      604/228
2013/0304021 A1* 11/2013 Cabiri ................ A61M 5/31511
                                                      604/506

* cited by examiner

FIG.15

SYRINGE ASSEMBLY

CROSS-REFERENCE TO RELATED APPLICATIONS

This is a U.S. national phase application under 35 U.S.C. § 371 of International Patent Application No. PCT/EP2016/065584, filed Jul. 1, 2016, and claims benefit of priority to European Patent Application No. 15306064.5, filed Jul. 1, 2015. The entire contents of these applications are hereby incorporated by reference.

FIELD OF TECHNOLOGY

The present invention concerns a syringe assembly having a hollow tubular syringe body, having a proximal end and a distal end, and a plunger rod, axially movable in the syringe body between an initial position and a final position.

BACKGROUND

In the field of fluid injection or extraction, it is known to provide a syringe assembly with a hollow tubular syringe body defining an inner chamber capable to be filled with a quantity of fluid.

It is known to place a movable plunger rod with a plunger being in contact in a fluid tight manner with the walls of the inner chamber of the syringe body to ensure the suction of the fluid in the hollow syringe body or the ejection of the fluid from the hollow syringe body. The plunger rod is slidable within the interior of the hollow syringe body between an initial position and a final position. Such a plunger rod is usually thin.

In the field of prefilled syringe assembly, it is known to add a temporary protection to the plunger rod to protect it during storage, while the plunger rod is in its initial position. The protection supports the plunger rod to avoid it to be bent. This protection is withdrawn before use.

SUMMARY

However, the withdrawal of the protection can be difficult for a non-trained operator.

Moreover, after the withdrawal of the protection, the plunger rod is no more supported during the injection. If the syringe is prefilled with a highly viscous component, the plunger rod can bend during injection and eventually be broken.

One of the goals of the invention is to overcome the above-mentioned drawback by preventing plunger rod bending during injection.

To this end, the invention relates to a syringe assembly of the afore-mentioned type, comprising:
 a support transversally stiff for supporting the plunger rod, the support having a distal end and a proximal end respectively transversally fixed to the syringe body and to the plunger rod, the proximal end of the support being movable with respect to the syringe body.

According to other features of the syringe assembly according to the invention:
 the distance between the distal end and the proximal end of the support is adjustable between a first length corresponding to the initial position of the plunger rod and a second length corresponding to the final position of the plunger rod;
 the proximal end of the support is jointly axially movable together with the plunger rod;
 the support is telescopic, the support comprising a first section and a second section, the first section being movable axially with respect to the second section and the sections having transverse bearing surfaces engaged together;
 the syringe comprises a lock for axially fixing the sections one with respect to another, the lock being movable between a locked position and an unlocked position, the first section being fixed axially relative to the second section when the lock is in the locked position, the first section being sliding axially relative to the second section, when the lock is in the unlocked position;
 the syringe comprises a window, wherein the lock presents a colored area with a color different from the rest of the section, the colored area being visible through the window only when the lock is in the locked position;
 the lock includes a bayonet mechanism;
 the lock is formed by a track on the outer wall of the first section and a protuberance on the inner wall of the second section;
 the lock is formed by a protuberance on the outer wall of the first section and by a track on the inner wall of the second section;
 the lock is rotationally movable between the locked position and the unlocked position and the assembly comprises a snap in window adapted to retain the protuberance so as to prevent the rotation of the lock;
 the support comprises a first section defining the proximal end, a second section and an third section defining the distal end, the second section being axially disposed between the first section and the third section, the first section being fixed in rotation with respect to the third section and the second section being movable in rotation with respect to the first section and to the third section to unlock the bayonet mechanism;
 the lock comprises an oblong portion having an outer wall presenting an oblong section along transversal plans, arranged in the first section and a complementary oblong recess defined on the inner wall of the second section and adapted to house the oblong portion, the first and second sections being rotationally movable;
 the oblong section is an elliptical section;
 the first section includes a cylindrical thrust collar axially connected to the oblong portion and in that the complementary oblong recess has partially a circular shape.

BRIEF DESCRIPTION OF DRAWINGS

Other aspects and advantages of the invention will appear upon reading the following description, given by way of example and made in reference to the appended drawings, wherein.

DETAILED DESCRIPTION

In the following description, the words "proximal" and "distal" mean respectively relatively closer from an operator and relatively distant from the operator, when the syringe assembly is in use.

In the following description, the word "longitudinal" is defined in reference to the main direction of the syringe assembly, the word "transversal" is defined in reference to any direction perpendicular to the longitudinal direction.

Two elements are "transversally fixed means that the stroke of an element with respect to another element is limited in all the transversal directions by the other element.

Referring to FIGS. 1 to 4, a syringe assembly 1 according to a first embodiment will be described.

Figure 1:
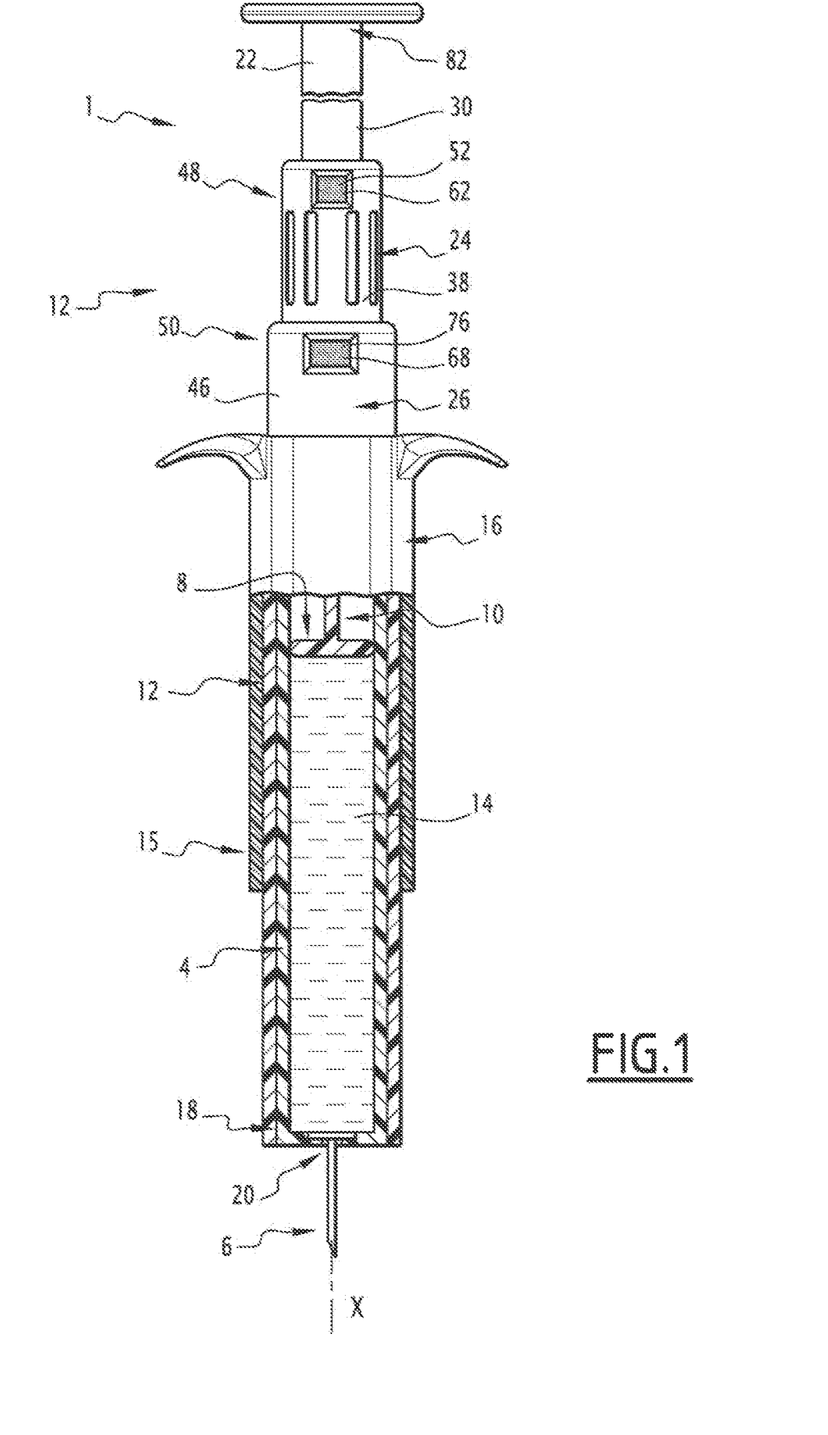
FIG. 1 is a partial cross-section view of a syringe assembly according to a first embodiment of the invention before injection.

The syringe assembly 1 is meant to inject a fluid in a body. For example, the fluid is a drug with a semi-solid formulation.

The syringe assembly 1 is elongated along a longitudinal axis X. The syringe assembly 1 comprises a syringe body 4, a needle 6, a plunger 8, a plunger rod 10 and a support 12 for supporting the plunger rod 10.

The syringe body 4 is hollow and tubular. The syringe body 4 defines an inner chamber 14. The inner chamber 14 is a reservoir for the fluid.

The syringe body 4 is covered by a dual sheath 15. As illustrated, the sheath 15 comprises a part with wing flanges for the syringe assembly 1 handling.

The syringe body 4 presents a proximal end 16 and a distal end 18. The distal end 18 of the syringe body 4 includes a seat 20 for the needle 6.

The needle 6 is arranged across the seat 20 of the distal end 18 of the syringe body 4. The inner diameter of needle 6 and the length of the needle 6 are adapted to the fluid to be injected.

The plunger 8 is in the inner chamber 14. The plunger 8 is meant to push the fluid toward the needle 6. The plunger 8 diameter is adapted to the diameter of the inner chamber 14. The plunger 8 is fluidtight. The plunger 8 is movable axially along the longitudinal axis X inside the inner chamber 14.

The plunger rod 10 is a shaft. The plunger rod 10 is mounted to push the plunger 8 in the inner chamber 14. The plunger rod 10 is joined together with the plunger 8. For example, the plunger 8 is integral with the plunger rod 10.

The length of the plunger rod 10 along the longitudinal axis X is for example . . . % the length of the syringe body 4. For example, the length of the plunger rod 10 is comprised between 5 cm and 20 cm. Moreover, the diameter of the plunger rod 10 in the transversal direction is substantially 50% smaller than the diameter of the inner chamber 14. The diameter of the plunger rod 10 is, for example, comprised between 2 mm and 8 mm.

The plunger rod 10 is, for example, made of plastic, metal or composite materials.

The plunger rod 10 is axially movable along the longitudinal axis X in the syringe body 4 between an initial position represented on FIG. 1 and a final position.

In the initial position, the plunger rod 10 extends mainly outward the syringe body 4. When the plunger rod 10 is in the initial position, the volume between the plunger 8 and the seat 20 of the needle 6 is maximal. This volume is, for example, filled with the fluid. The initial position corresponds to a prior-to injection position.

In the final position, the plunger rod 10 extends mainly inside the inner chamber 14. When the plunger rod 10 is in the final position, the plunger 8 comes into contact with the seat 20 of the needle 6. The final position corresponds to an end-of injection position.

The part of the plunger rod 10 which is not extending in the syringe body 4 is surrounded by the support 12. The support 12 is adapted to prevent bending of the plunger rod 10 all along the stroke of the plunger rod 10.

Figures 2, 3:
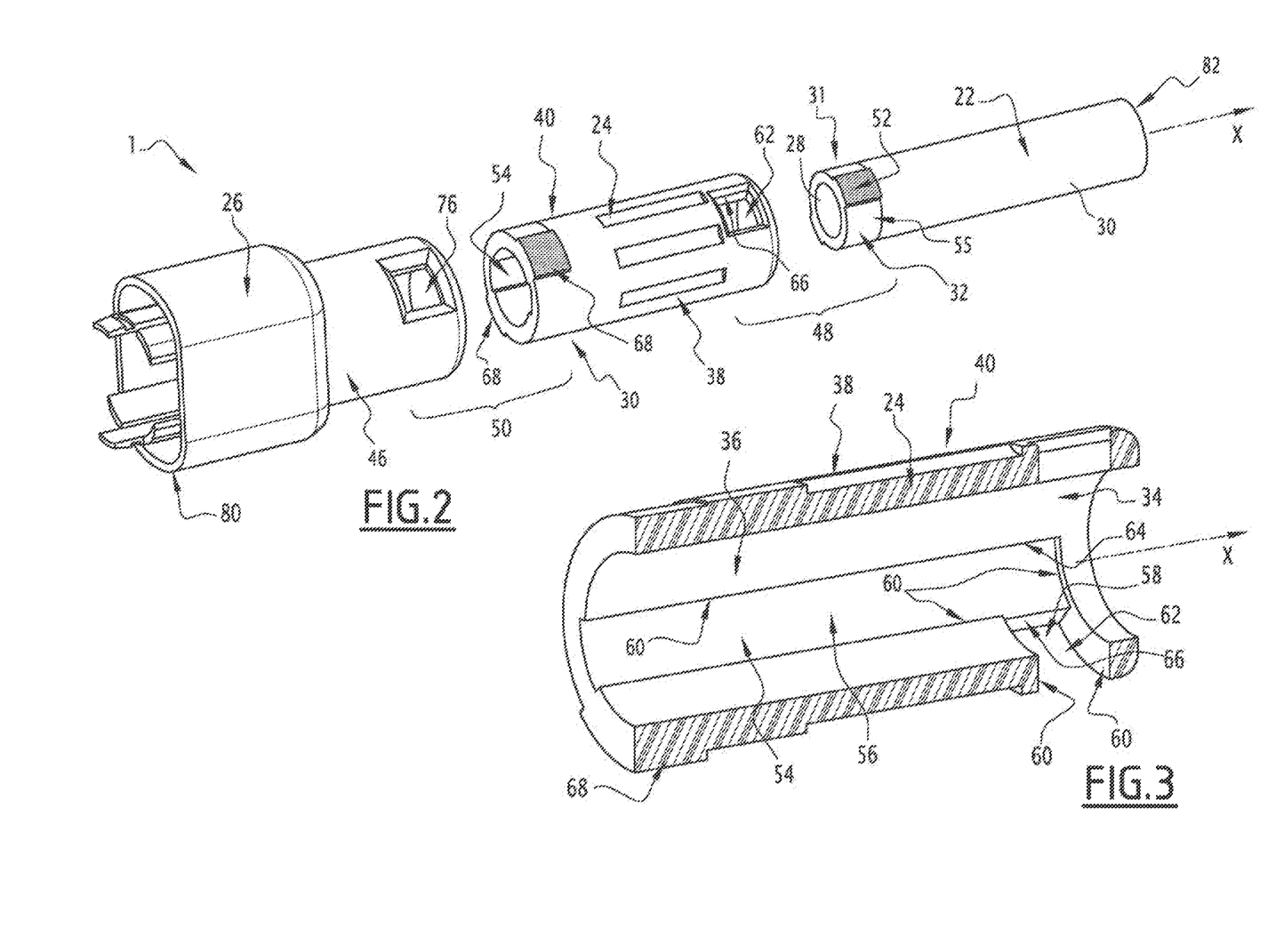
FIG. 2 is an exploded view of the support of the syringe assembly of FIG. 1.
FIG. 3 is a cross section view of the distal section of the support of FIG. 2.

The support 12 is telescopic, as illustrated in FIG. 2. It means that the support 12 comprises at least a first and a second section, the second section being movable axially with respect to the first section. The telescopic support 12 is maneuverable between a deployed position and a retracted position.

In the examples represented, the support 12 comprises three tubular sections: a proximal section 22, an intermediate section 24 and a distal section 26. Each section 22, 24, 26, is hollow and tubular. The distal section 26 is fixed axially with the syringe body 4. The intermediate section 24 is transversally fixed to the distal section 26 and movable inside the distal section 26. The proximal section 22 is transversally fixed to the intermediate section 24 and movable inside the intermediate section 24.

The proximal section 22 presents an inner wall 28 and an outer wall 30.

The inner diameter of the proximal section 22 is large enough to receive the plunger rod 10.

The proximal section 22, represented on FIG. 2, is internally movable axially along the longitudinal axis X with respect to the intermediate section 24 represented on FIGS. 2 and 3.

The proximal section 22 comprises an outer thrust collar 31, at the distal end of the proximal section 22. The outer thrust collar 31 extends radially from the outer wall 30 of the proximal section 22.

The difference between the thickness of the thrust collar 31 and the thickness of the proximal section 22 measured between the inner wall 28 and the outer wall 30 is for example inferior to 100 µm.

The whole outward face of the thrust collar 31 is an outer bearing surface 32 intended to face an inner bearing surface 34 of the intermediate section 24.

The inner diameter of the intermediate section 24 is large enough to receive the proximal section 22 and to allow its translation along the longitudinal axis X.

The intermediate section 24 presents an inner wall 36 and an outer wall 38. The inner bearing surface 34 of the intermediate section 24 is defined on the inner wall 36 of the intermediate section 24.

The inner diameter of the intermediate section 24 is larger than the outer diameter of thrust collar 31. The diameters are adapted to allow receiving of the proximal section 22 in the intermediate section 24 and translation of the proximal section 22 along the longitudinal axis X inside the intermediate section 24. The translation of the proximal section 22 with respect to the intermediate section 24 is guided along the facing bearing surfaces 32, 34 of both sections 22, 24. The proximal section 22 and the intermediate section 24 are tight fitted in the areas of their facing bearing surfaces 32, 34. The backlash between the sections 22, 24 in the bearing surfaces 32, 34 areas is adapted to allow axially sliding and guiding of the proximal section 22 in respect with the intermediate section 24. Moreover the backlash is adapted to create a resistance during the translation. The backlash between the sections 22, 24 in the bearing surfaces 32, 34 areas is lower than 50 μm.

Figure 4:
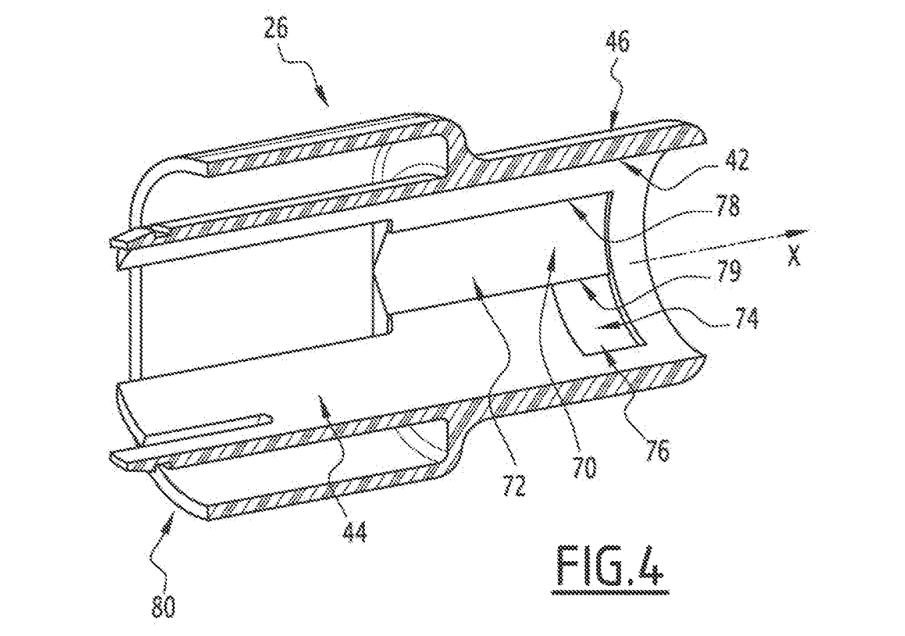
FIG. 4 is a cross section view of the intermediate section of the support of FIG. 2.

The intermediate section 24 is internally movable axially along the longitudinal axis X with respect to the distal section 26, represented on FIGS. 2 and 4.

Another outer bearing surface 40 is defined on the outer wall 38 of the intermediate section 24. The outer bearing surface 40 is facing an inner bearing surface denoted 42 of the distal section 26.

The outer wall 38 of the intermediate section 24 also comprises stripes to facilitate the handling of this section 24.

The distal section presents an inner wall 44 and an outer wall 46.

The inner bearing surface 42 of the distal section 26 is defined on the inner wall 44 of the distal section 26.

The outer wall 46 of the distal section 26 is partially covered by the sheath 15 as illustrated on FIG. 1.

The inner diameter of the distal section 26 is larger than the outer diameter of the intermediate section 24. The diameters are adapted to allow receiving of the intermediate section 24 in the distal section 26 and translation of the intermediate section 24 along the longitudinal axis X inside the distal section 26. The translation of the intermediate section 24 with respect to the distal section 26 is guided along the facing bearing surfaces 40, 42 of both sections 24, 26. The intermediate section 24 and the distal section 26 are tight fitted in the area of their facing bearing surfaces 40, 42. The backlash between the sections 24, 26 in the bearing surfaces 40, 42 areas is adapted to allow axially sliding and guiding of the intermediate section 24 in respect with the distal section 26. Moreover the backlash is adapted to create a resistance during the translation. The backlash between the sections 24, 26 in the bearing surfaces 40, 42 areas is lower than 50 μm.

The facing bearing surfaces 32, 34; 40, 42 prevent the support 12 from bending. The support 12 is transversally stiff. It means that the support 12 cannot be bent in a transversal direction with a force inferior to a force of 50 N.

The facing bearing surfaces 32, 34; 40, 42 are disposed around the whole periphery of their respective section to avoid bending of the support 12 in any transversal direction.

The syringe assembly 1 further comprises a first lock 48 and a second lock 50 to lock axially the different sections 22, 24, 26.

The first lock 48 is movable between a locked position and an unlocked position. The proximal section 22 is fixed axially relative to the intermediate section 24 when the first lock 48 is in the locked position. The proximal section 22 is slidable axially along the longitudinal axis X relative to the intermediate section 24, when the first lock 48 is in the unlocked position.

The first lock 48 includes a bayonet mechanism between the proximal section 22 and the intermediate section 24. A bayonet mechanism is formed by at least a protuberance cooperating with an associated track.

The proximal section 22 comprises two diametrically opposite first protuberances 52 collaborating with two diametrically opposite first tracks 54 formed in the inner bearing surface 34 of the intermediate section 24. Only one first track is represented on FIGS. 2 and 3. To simplify the description only a track 54 and a protuberance 52 of the first lock 48 will be described.

The two first protuberances 52 extend radially outward from a base surface 55 of the thrust collar 31.

The first track 54 shape is adapted to fit the first protuberance 52 and to guide its rotation about the longitudinal axis X and its translation along the longitudinal axis X. The first track 54 is an L-shaped track. The first track 54 presents a longitudinal portion 56 and an orthoradial portion 58. The first track 54 is a groove delimited by walls 60.

The longitudinal portion 56 is elongated along the longitudinal direction X. The longitudinal portion 56 is open at its distal end and closed by a wall 60 at its proximal end.

The orthoradial portion 58 extends from the proximal end of the longitudinal portion 56, perpendicularly to the longitudinal direction X and perpendicularly to a radial direction. A radial direction is a transversal direction that cuts the longitudinal axis X. The orthoradial portion 58 comprises at one end a first window 62 and at the other end an alignment abutment 64.

The deepness and width of the first track 54 in the longitudinal portion 56 are adapted so that the walls 60 prevent radial movement of the first protuberance 52 in the longitudinal portion 56. Similarly, the deepness and width of the first track 54 in the orthoradial portion 58 are adapted so that the walls 60 prevent longitudinal movement of the first protuberance 52 in the orthoradial portion 58.

Furthermore, the wall 60 at the proximal end of the track 54 is an abutment limiting the translation stroke of the proximal section 22 along the longitudinal axis X with respect to the intermediate section 24.

When the first protuberance 52 is in the orthoradial portion 58 of first the track 54, the first lock 48 is in the locked position. When the first protuberance 52 is in the longitudinal portion 56 of the first track 54, the first lock 48 is in the unlocked position.

Advantageously the first window 62 is a snap in window for retaining the protuberance 52. The snap in window 62 is a part of an anti-rotation mechanism preventing untimely unlocking of the first lock 48. The anti-rotation mechanism is a snap in mechanism.

The first protuberance 52 presents a shape fitting to the first window 62. When the first protuberance 52 is snapped in the first window 62, the first lock 48 is maintained in the locked position, and will not rotate untimely. The torque to unlock the first lock 48 with a rotation is higher than 20 N.m.

The distance between the longitudinal axis X and the apex of the first protuberance 52 is higher than the distance between the longitudinal axis X and an edge 66 of the first window 62. The difference between the distances is less than 50 μm. The edge 66 forms a radial stop retaining the protuberance 52.

Moreover, the window 62 also provides an indication about if the proximal section 22 is axially locked with respect to the intermediate section 24 or unlocked. Advantageously, the outward surface of the protuberance 52 is in a color different from the outward surface of the base surface 55 of the thrust collar 31.

The second lock 50 is similar to the first lock 48. The second anti-rotation mechanism is similar to the first anti-rotation mechanism.

The second lock 50 comprises two diametrically opposite second protuberances 68 placed on the distal end of the intermediate section 24 and two diametrically opposite second tracks 70 on the inner wall 44 of the distal section 26. Each second track 70 presents a longitudinal portion 72 and an orthoradial portion 74. The orthoradial portion 74 comprises a second window 76 and a second abutment 78. The second window 76 comprises an edge 80 similar to the edge 66.

The orthoradial portion 74 of the second track 70 extends from the longitudinal portion 72 in the same direction as the orthoradial portion 58 of the first track 54 extends from the longitudinal portion 56.

When both the first lock 48 and the second lock 50 are in their respective locked position, the support 12 prevents any axial movement along the longitudinal axis X of the plunger rod 10.

The distal end 80 of the distal section 26, represented on FIGS. 2 and 4 is transversally fixed to the proximal end 16 of the syringe body. The distal end 80 of the distal section 26 is the distal end of the support 12.

The proximal end 82 of the support is the proximal end of the proximal section 22.

The proximal end 82 of the support 12 is movable with respect to the syringe body 4. The proximal end 82 is jointly axially movable together with the plunger rod 10.

When the plunger rod 10 is in the initial position, the support 12 is deployed.

When the support 12 is retracted, the proximal section 22 is completely in the intermediate section 24 which is completely in the distal section 26.

The distance between the distal end 80 and the proximal end 82 of the support 12 is adjustable between a first length corresponding to the initial position of the plunger rod 10 and a second length corresponding to the final position of the plunger rod 10. The first length is the length of the support 12 when the support 12 is deployed. The second length is the length of the support 12 when the telescopic support 12 is retracted.

The assembly method of the support 12 of the syringe assembly 1 according to the first embodiment of FIGS. 2 to 4 will now be described.

First, the intermediate section 24 is inserted in the distal end of the distal section 26. The intermediated section 24 is inserted so as the second protuberance 68 are aligned with the second track 70 in front of the opening of the second track 70. The proximal end of the intermediate section 24 is pushed inside the distal section 26.

The second protuberance 68 slides inside the longitudinal portion 72. When the second protuberance 68 is in the orthoradial portion 74, the intermediate section 24 is rotated from the alignment abutment 78 position to the second window 76. When the second protuberance 68 is in the second window 76, it is locked. The second lock 50 is in the locked position.

Then the proximal section 22 is inserted in the distal end of the intermediate section 24 inside the distal section. The proximal section 22 is inserted so as the first protuberance 52 is aligned with the first track 54 in front of the opening of the first track 54. The first protuberance 52 slides inside the longitudinal portion 56. When the first protuberance 52 is in the orthoradial portion 58, the proximal section 22 is rotated from the alignment abutment 64 to the first window 62. When the first protuberance 52 is in the first window 62, it is locked. The first lock 48 is in the locked position.

The method of injection with the syringe assembly 1 according to the first embodiment 1 will now be described.

A syringe assembly 1 is provided with the inner chamber 14 filled with a fluid to inject, with the plunger rod 10 in the initial position and the locks 48, 50 in the locked position and snapped in the windows 62, 76.

During storage, the unlocking of the support 2 is prevented when each protuberance 52, 68 is snapped in the respective window 62, 76 so the plunger rod 10 translation is prevented.

There is unlocking steps before the injection.

During a first unlocking step, the bayonet mechanism of the second lock 50 is twisted to allow movement of the intermediate section 24 inside the distal section 26. The intermediate section 24 is rotated by the user relatively to the distal section 26. During the rotation, the second protuberance 68 is released form the second window 76 and slides along the orthoradial portion 74 of the second track 70. The second protuberance 68 is placed on the alignment abutment position 78 at the beginning of the longitudinal portion 72 of the second track 70. During this rotation of the intermediate section 24, the wall 60 of the orthoradial portion 58 opposite to the longitudinal portion 56 is abutting and pushing the first protuberance 50. So the rotation of the intermediate section 24 entrains simultaneously the rotation of the proximal section 22 relatively to the distal section 26. The proximal section 22 remains locked to the intermediate section 24.

At the end of this rotation, the user can visualise through the second window 76, that the second lock 50 is unlocked, and through the first window 62 that the first lock 48 is still locked. Indeed before rotation, the outward surface of the protuberance 52, 68 were facing both window 62, 76 and after rotation a colored area of the intermediate section 24 is facing the second window 76. It provides an indication about the position of the lock 48, 50.

Then, during a second unlocking step, the bayonet mechanism of the first lock 48 is twisted on the other direction to allow movement of the proximal section 22 of the support 12. The proximal section 22 is rotated by the user relatively to the intermediate section 24 in a direction opposite to the first unlocking step. During the rotation, the first protuberance 52 is released from the first window 62 and slides along the orthoradial portion 56 of the first track 54. The first protuberance 52 is placed on the alignment abutment position 64 at the beginning of the longitudinal portion 56 of the first track 54

Similarly, at the end of rotation, instead of the outward surface of the first protuberance 52 facing the first window 62, the base surface 55 of the thrust collar 31 is facing the first window 62, indicating to the user that the first lock 48 is unlocked.

The rotations of the protuberance 52, 68 toward the longitudinal portion 56, 66 unlock axially the support 12 so the plunger rod 10 becomes movable with the support 12.

During injection the user presses the proximal end 82 of the support 12 to move it from its deployed position to its retracted position. The user presses only the proximal section 22 of the support 12. The proximal section 22 is sliding inside the intermediate section 24 and the intermediate section 24 is sliding inside the distal section 26.

As the proximal end 82 of the support 12 is sliding along the longitudinal axis X, the plunger rod 10 is moving inside the syringe body 4 from its initial position to its final position. The plunger 8 is pushed toward the seat 20 of the needle 6 and the fluid is ejected through the needle 6.

As the plunger rod 10 is pushed, each protuberance 52, 68 moves along its respective track 54, 70 until the support 12 is in retracted position. When the support 12 is in its retracted position, the plunger 8 is in its final position and the whole quantity of fluid has been injected.

A second embodiment of the syringe assembly 100 will now be described in reference to FIGS. 5 to 8. The syringe assembly according to the second embodiment 100 differs from the syringe assembly according to the first embodiment 1 in that lock 102, 104 features are different.

Figure 5:
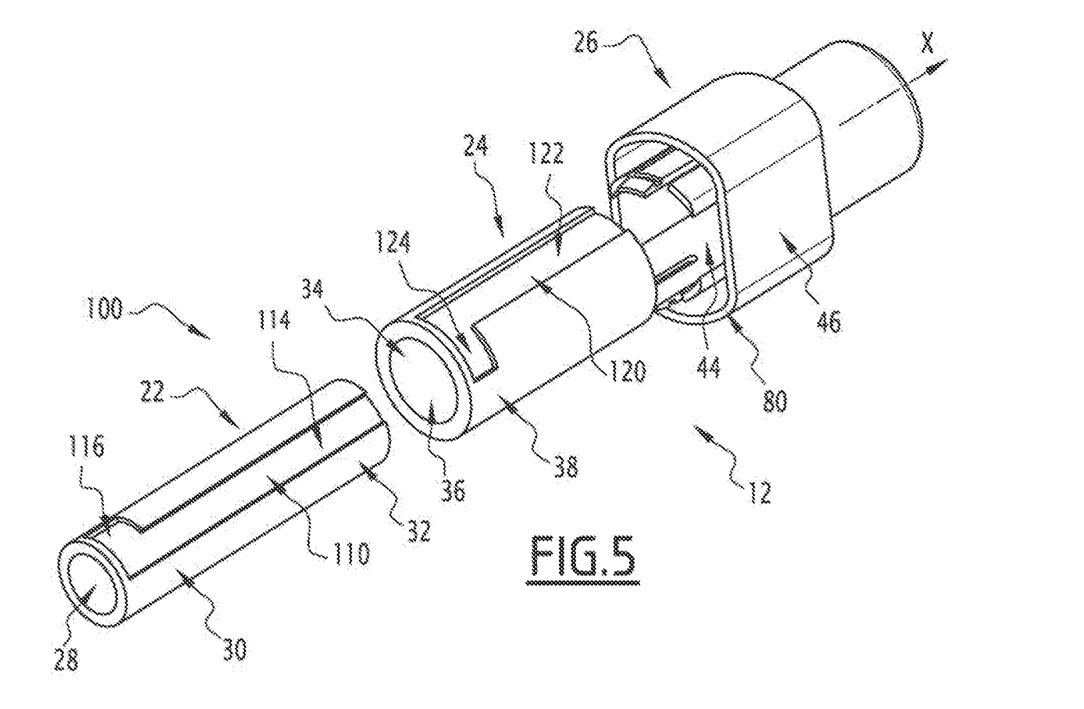
FIG. 5 is an exploded view of a support of a syringe assembly according to a second embodiment of the invention.

The outer bearing surface 32 of the proximal section 22, shown on FIG. 5, intended to face the inner bearing surface 34 of the intermediate section 24, is defined on the outer wall 30 of the proximal section 22. The inner bearing surface 34 of the intermediate section 24 is defined on the inner wall 36 of the intermediate section 24.

Figure 6:
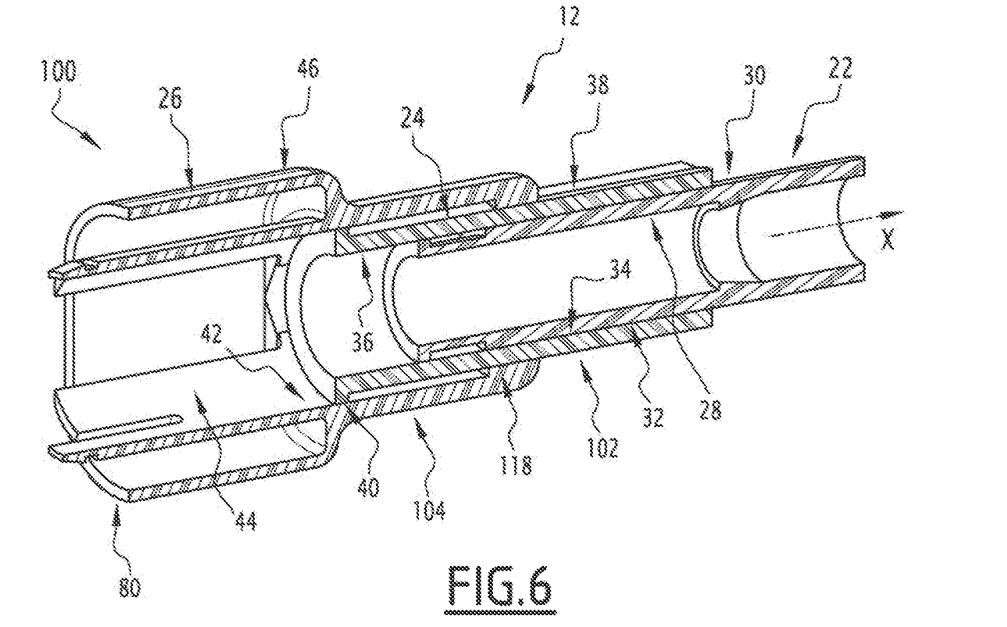
FIG. 6 is a cross section view of the support of FIG. 5.

The outer bearing surface 40 defined on the outer wall 38 of the intermediate section 24 is intended to face the inner bearing surface 42, shown on FIG. 6, defined on the inner wall 44 of the distal section 26.

The first lock 102, shown on FIG. 6, is formed by a first track 110, shown on FIG. 5, defined on the outer wall 30 of the proximal section 22 and a first protuberance, not represented, on the inner wall 36 of the intermediate section 24.

The first track 110 comprises a longitudinal portion 114 and an orthoradial portion 116 shown on FIG. 5. The orthoradial portion 116 extends perpendicularly from the distal end of the longitudinal portion 114.

Similarly, the second lock 104, shown on FIG. 6, comprises a second protuberance 118, on the inner wall 44 of the distal section 26 and a second track 120 on the outer wall 38 of the intermediate section 24. The second track 120, shown on FIG. 5, comprises a longitudinal portion 122 and an orthoradial portion 124 extending from the distal end of the longitudinal portion 122.

The orthoradial portion 124 of the second track 120 extends from the longitudinal portion 122 in a direction opposite to the direction in which the orthoradial portion 116 of the first track 110 extends from the longitudinal portion 114 of the first track 110.

Each protuberance 118 extends radially inward.

The syringe assembly according to the second embodiment 100 also differs from the syringe assembly according to the first embodiment in that the plunger rod is fixed in rotation to the proximal section 22 and to the distal section 26.

Therefore the proximal section 22 is fixed in rotation relatively to the distal section 26 because of the plunger rod 10.

Figure 7:
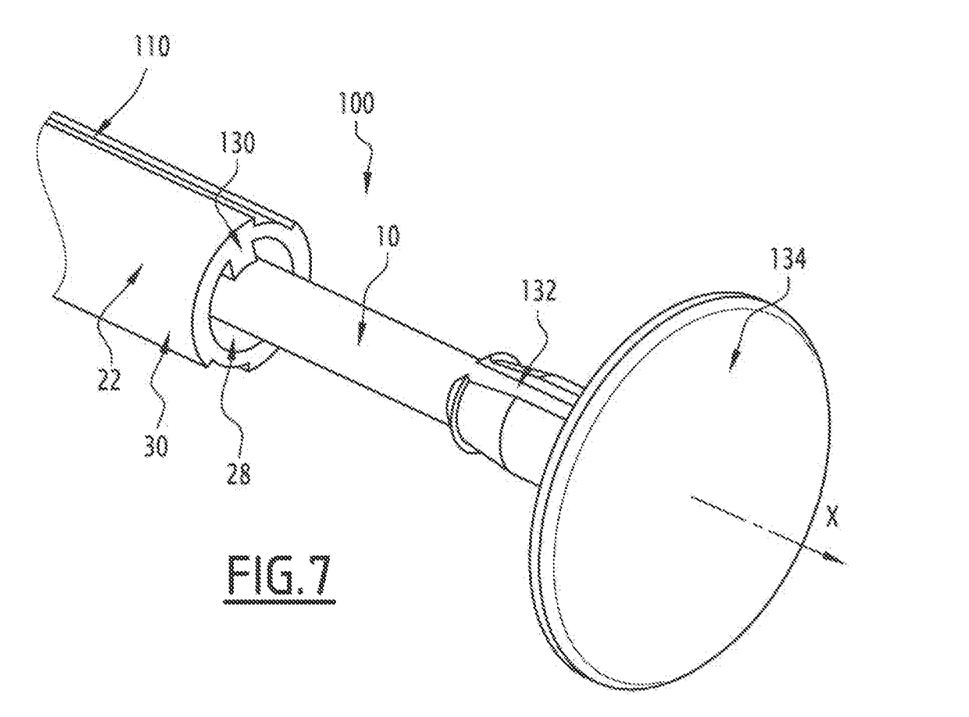
FIG. 7 is a view of a part, represented unassembled, of the syringe assembly according to the second embodiment of the invention.

As illustrated on FIG. 7, the plunger rod 10 is keyed to the proximal end of the proximal section 22 of the support 12. For example, the proximal section 22 of the support 12 comprises, on its inner wall 28, an internal rib 130. The rib 130 extends along the longitudinal axis X. The plunger rod 10 comprises a groove 132 fastenable with the rib 130 to prevent rotation of the plunger rod 10 relatively to the proximal section 22.

A similar rotation locking system is provided between the distal section 26 and the plunger rod 10.

Figure 8:
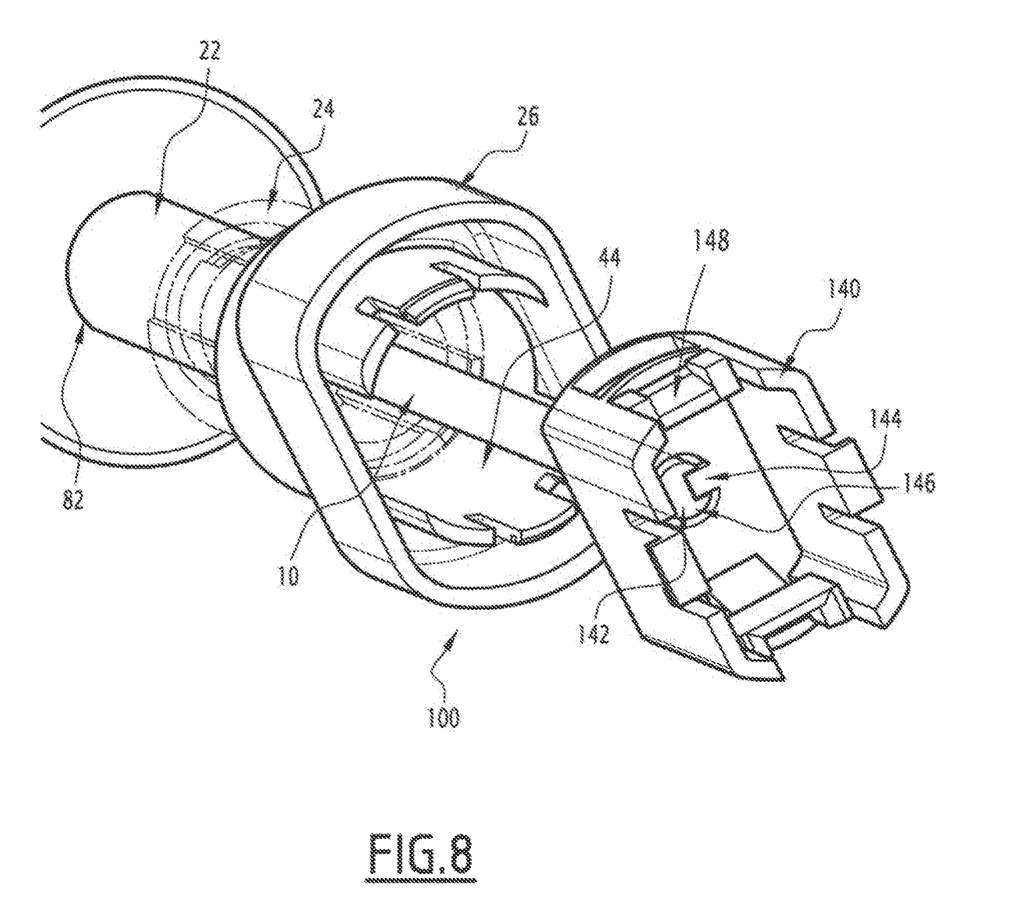
FIG. 8 is a view of another part, represented unassembled, of the syringe assembly according to the second embodiment of the invention.

The syringe assembly 100 comprises an insert element 140 assembled in the distal section 26 as illustrated on FIG. 8.

The insert element 140 comprises a hole 142 in which is engaged the plunger rod 10. The hole 142 presents a rib 144 cooperating with a distal groove 146 of the plunger rod 10. The rod 10 is movable in translation along the longitudinal axis X through the hole 142.

The external shape of the insert element 140 prevents its rotation inside the distal section 26. Furthermore, the insert element 140 comprises snap in mechanism 148 to be fixed to the distal section 26.

The method of injection with the syringe assembly 100 according to the second embodiment differs from the method of injection of the syringe assembly according to the first embodiment in that there is just one unlocking step.

During the unlocking step, the intermediate section 24 is manually rotated. The proximal section 22 does not rotate relatively to the distal section 26 because the rotation is prevented by the plunger rod 10.

During the rotation of the intermediate section 24, the first protuberance slides in the first orthoradial portion 116 of the first track and the second protuberance slides in the first orthoradial portion of the second track so both locks are unlocked simultaneously.

A third embodiment of the syringe assembly 160 will now be described in reference to FIGS. 9 to 15.

The syringe assembly according to the third embodiment 160 differs from the syringe assembly according to the second embodiment 100 in that it comprises different lock 162, 164, the sections 22, 24, 26 being still tubular.

The outer bearing surface 32 of the proximal section 22 intended to face the inner bearing surface 34 of the intermediate section 24, is defined on the outer wall 30 of the proximal section 22. The inner bearing surface 34 of the intermediate section 24 is defined on the inner wall 36 of the intermediate section 24.

The outer bearing surface 40 defined on the outer wall 38 of the intermediate section 24 is intended to face the inner bearing surface 42 defined on the inner wall 44 of the distal section 26.

Figure 9:
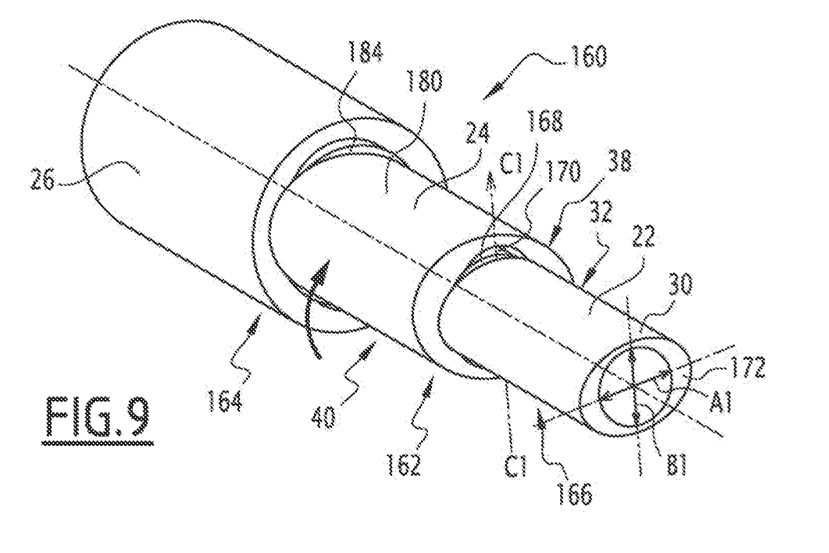
FIGS. 9 to 11 are views of a support of a syringe assembly according to a third embodiment during successive unlocking steps.
Figure 10:
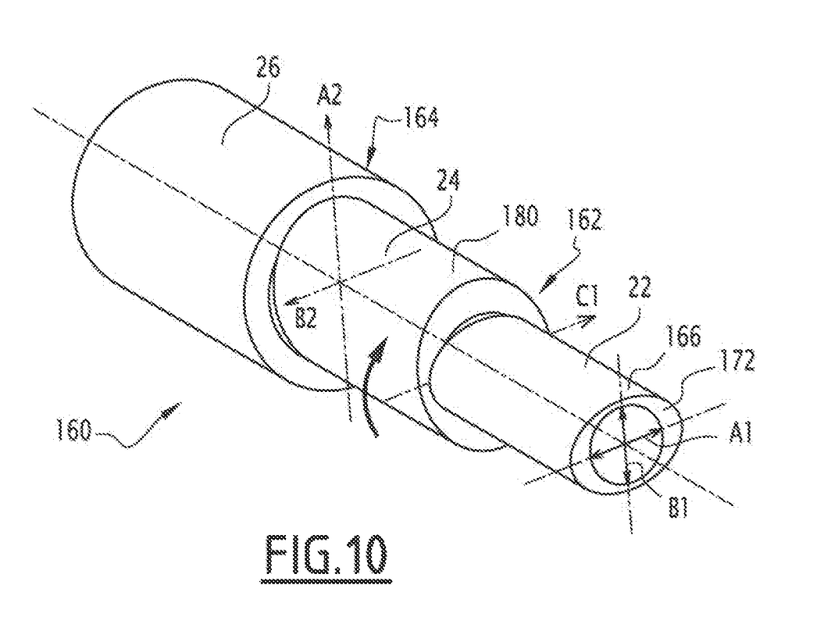
Figure 11:
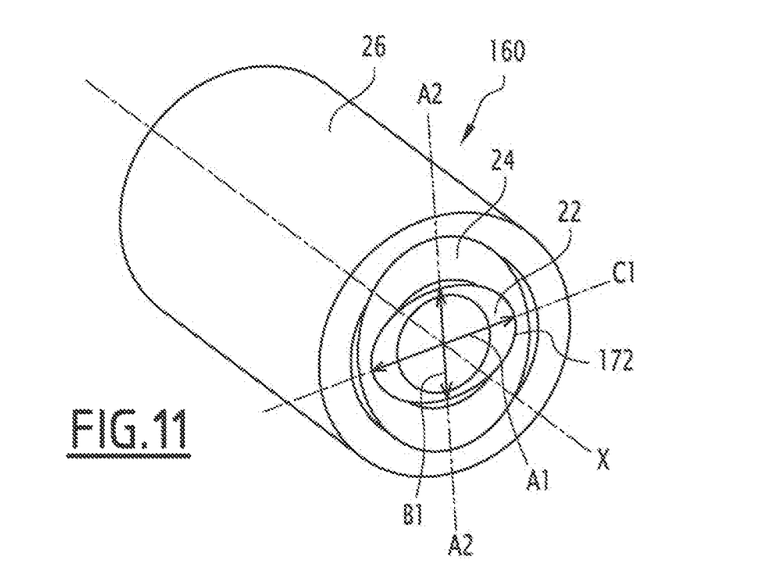

As illustrated on FIGS. 9 to 11, the proximal section 22 comprises an oblong portion wherein the outer wall presents an oblong section along transversal plans, and a first cylindrical thrust collar 168 wherein the outer wall 30 presents a circular section along transversal plans. In the example, the oblong portion is an elliptical portion 166 and the oblong section is an elliptical section along transversal plans The elliptical portion 166 and the first thrust collar 168 are coaxially connected.

Figure 12:
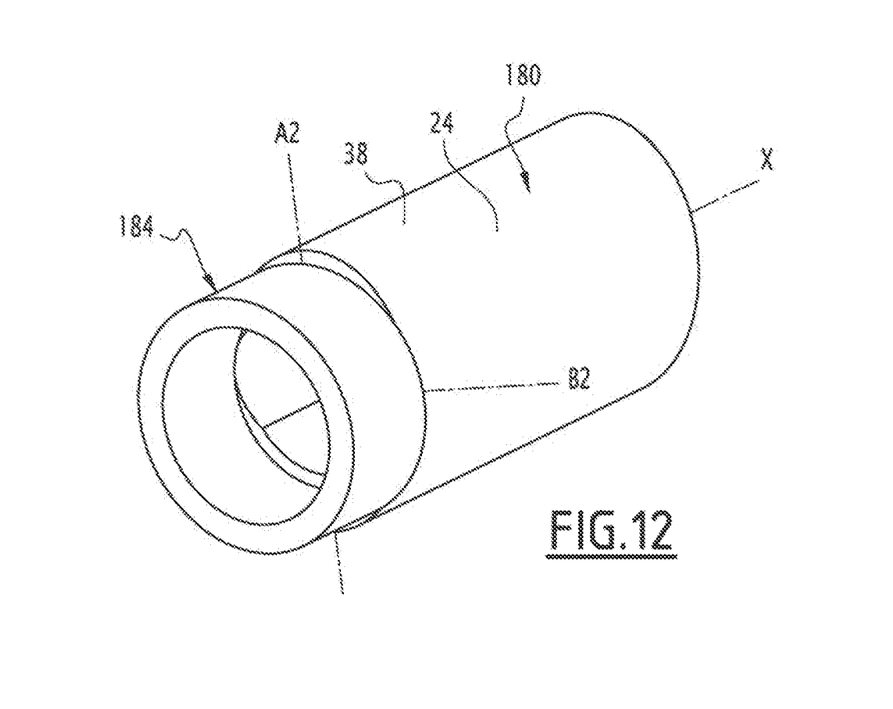
FIG. 12 is a view of a part, represented unassembled, of the syringe assembly according to the third embodiment.
Figures 13, 14, 15:
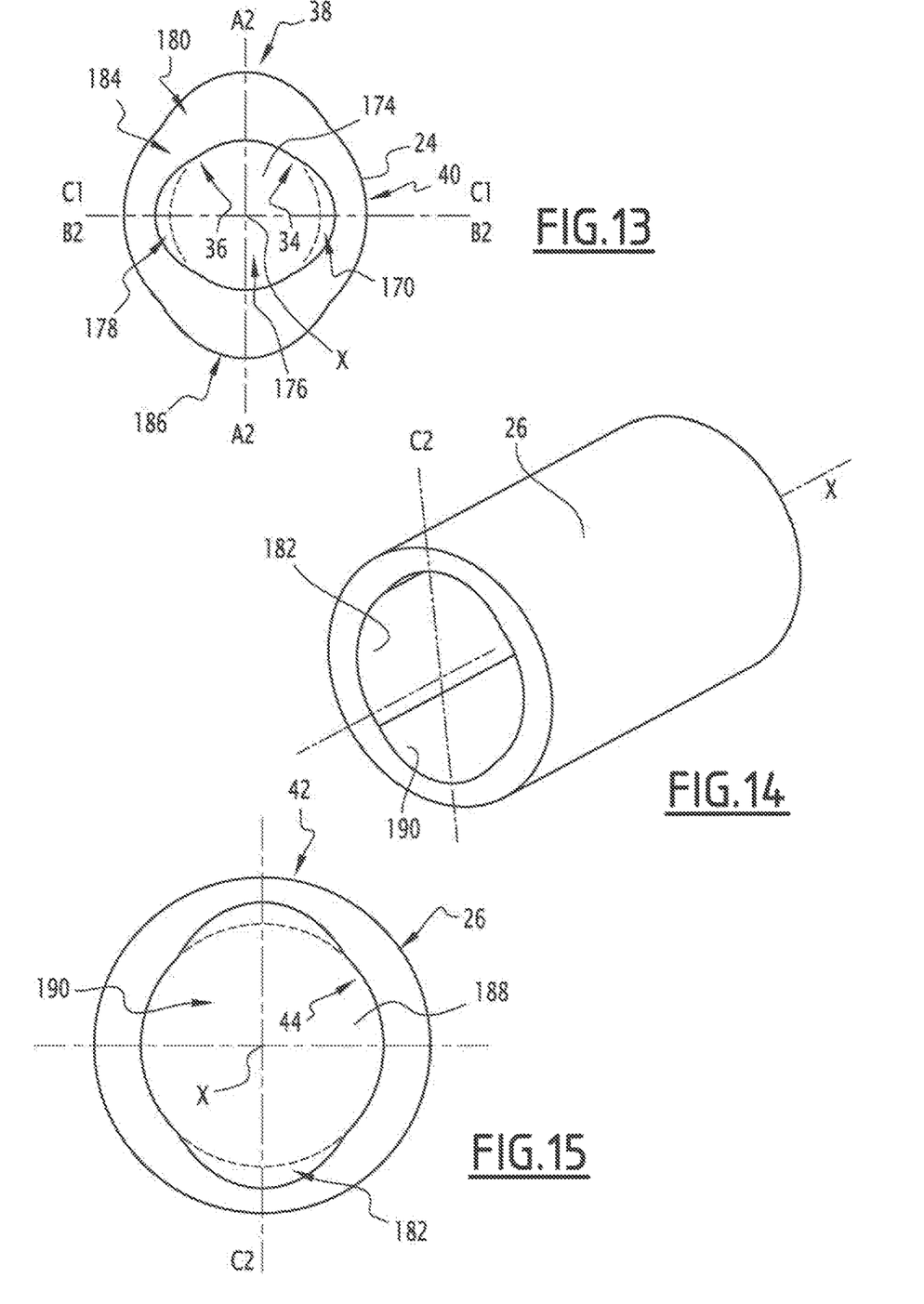
FIG. 13 is a transversal view of the part of FIG. 12.
FIG. 14 is a view of another part, represented unassembled of the syringe assembly according to the third embodiment.
FIG. 15 is a transversal view of the part of FIG. 14.

The first lock 162 is formed by the first elliptical portion 166 defined on the outer wall 30 of the proximal section 22 and a first elliptical recess 170 shown on FIGS. 12 and 13 defined on the inner wall 36 of the intermediate section 24.

The first elliptical portion 166 defines a first ellipse 172 along transversal plans. The center of the first ellipse 172 is positioned on the longitudinal axis X. The first ellipse 172 is elongated along a first major axis A1 perpendicular to the longitudinal axis X. The first ellipse presents a first minor axis B1 perpendicular to the first major axis A1 and perpendicular to the longitudinal axis X and passing through the center.

The inner wall 36 of the intermediate section 24 presents a profile 174 adapted to allow free rotation of the first thrust collar 168 of the proximal section 22 but to cooperate with the first ellipse 172 only in one angular position.

As shown on FIG. 13, the inner profile 174 defines a substantially circular hole 176 presenting the first elliptical recesses 170. The elliptical recesses 170 extend from the circular hole 176 along a first alignment axis C1.

The internal circular hole 176 cooperating with the associated thrust collar 168 keeps both sections 22, 24 concentric and centered on the longitudinal axis X.

The circular hole 176 is complementary to the thrust collar 31. The outer diameter of the thrust collar 168 is slightly smaller to the diameter of the circular hole 176. The difference between the diameters is less than 50 µm.

The elliptical recesses 170 of the inner profile 174 are complementary to the first ellipse 172, when the major axis A1 of the ellipse 172 is aligned with the alignment axis C1. The dimension of the first ellipse 172 along the major axis A1 is equal to the longest distance between the elliptical recesses 170 measured along the first alignment axis C1.

Similarly, the second lock 164 is formed by a second elliptical section 180 defined on the outer wall 38 of the intermediate section 24 and a second elliptical recess 182 defined on the inner wall 44 of the distal section 26, represented on FIG. 15.

As illustrated on FIG. 12, the intermediate section 24 comprises the second elliptical portion 180 wherein the outer wall 38 presents an elliptical section along transversal plans and a second cylindrical thrust collar 184 wherein the outer wall 38 presents a circular section along transversal plans.

The second elliptical portion 180 defines a second ellipse 186 along transversal plans, presenting a second major axis A2 and a second minor axis B2 perpendicular to the second major axis A2 and perpendicular to the longitudinal axis X and passing through the center of the second ellipse 186 positioned on the longitudinal axis X, as represented on FIG. 13.

Moreover the second major axis A2 is perpendicular to the alignment axis C1 of the first elliptical recesses 170 defined by the inner wall 38 of the intermediate section 24.

As represented on FIGS. 14 and 15, the inner wall of the distal section 26 presents an inner profile 188 adapted to allow free rotation of second thrust collar 184 of the intermediate section 24 but to cooperate with the second ellipse 186 only in one angular position. The inner profile 188 defines a substantially circular hole 190 presenting the second elliptical recesses 182 extending along a second alignment axis C2.

The method of injection with the syringe assembly 160 according to the third embodiment will now be described.

During the unlocking step, the intermediate section 24 is manually rotated. This intermediate section 24 is allowed to rotate because the second thrust collar 184 is engaged in the circular hole 190 of the distal section 26 and the circular hole 176 of the intermediate section 24 is cooperating with the first thrust collar 168.

As shown on FIGS. 9 to 10, the intermediate section 24 rotates so that the major axis A1, A2 of each ellipse 174, 186 is aligned with the associated alignment axis, C1, C2.

Each ellipse 174, 186 needs to be aligned with the associated elliptical recesses 170, 182 to allow the translation of a section in another section. Both locks are unlocked simultaneously.

Then, when the user presses on the proximal end of the syringe assembly 160, the proximal section 22 slides inside the intermediate part 24 and the intermediate section 24 slides inside the distal section 26.

The syringe assembly 1, 100 according to the invention is robust and easy to use.

The plunger rod 10 is transversally supported by the support 12 along the whole stroke of the plunger 8. It prevents bending and breaking of the plunger rod 10 during storage and during injection.

Moreover the bearing surfaces 32, 34, 40, 42 between the different sections 22, 24, 26 allow having a high transversal stiffness of the support 12 even if the support 12 is telescopic.

Moreover as the user does not need to remove the support 12 before injection, the use of this syringe assembly 1 is simplified.

The lock 48, 50, 102, 104 allows an improvement of security of the syringe assembly. If the lock 48, 50, 102, 104 is not rotated to the unlocked position, the plunger 8 stays in its position prior to and after drug delivery.

It prevents the syringe assembly 1, 100 from being used in an untimely manner. The unlocking of the plunger rod 10 is simple.

Alternatively, there is another locking step after the injection.

Advantageously another safety mechanism is activated when the rod is in its final position. The safety mechanism is, for example, a mechanism to retract the needle and to prevent further movement of the support 12.

Alternatively, the proximal section 22 of the first syringe assembly 1 is fixed in rotation relatively to the plunger rod 10. For example, the rotation of the proximal section 22 is prevented by a similar system as the one illustrated on FIG. 7.

Alternatively, the plunger rod 10 of the first syringe assembly 1 is fixed in rotation relatively to the distal section 26 and consequently to the syringe body 4. For example, the rotation of the plunger rod is prevented by an insert element similar to the insert element 140 illustrated on FIG. 8.

The invention claimed is:

1. A syringe assembly comprising:
a hollow tubular syringe body, having a proximal end and a distal end,
a plunger rod, axially movable in the syringe body between an initial position and a final position,
wherein the syringe assembly comprises:
a support transversally stiff for supporting the plunger rod, the support having a distal end and a proximal end respectively transversally fixed to the syringe body and to the plunger rod, the proximal end of the support being movable with respect to the syringe body,
wherein the distance between the distal end and the proximal end of the support is adjustable between a first length corresponding to the initial position of the plunger rod and a second length corresponding to the final position of the plunger rod,
wherein the support is telescopic, the support comprising a first section and a second section, the first section being movable axially with respect to the second section and the sections having transverse bearing surfaces engaged together,
the syringe assembly further comprising a lock for axially fixing the sections one with respect to another, the lock being movable between a locked position and an unlocked position, the first section being fixed axially-relative to the second section in both axial directions when the lock is in the locked position, the first section being sliding axially relative to the second section, when the lock is in the unlocked position,
wherein the lock includes a bayonet mechanism.

2. A syringe assembly according to claim 1, wherein the proximal end of the support is jointly axially movable together with the plunger rod.

3. A syringe assembly according to claim 1, comprising a window, wherein the lock presents a colored area with a color different from the rest of the section, the colored area being visible through the window only when the lock is in the locked position.

4. A syringe assembly according to claim 1, wherein the lock is formed by a track on the outer wall of the first section and a protuberance on the inner wall of the second section.

5. A syringe assembly according to claim 1, wherein the lock is formed by a protuberance on the outer wall of the first section and by a track on the inner wall of the second section.

6. A syringe assembly according to claim 4, wherein the lock is rotationally movable between the locked position and the unlocked position and the assembly comprises a snap in window adapted to retain the protuberance so as to prevent the rotation of the lock.

7. A syringe assembly according to claim 5, wherein the lock is rotationally movable between the locked position and the unlocked position and the assembly comprises a snap in window adapted to retain the protuberance so as to prevent the rotation of the lock.

8. A syringe assembly according to claim 1, wherein the support comprises a first section defining the proximal end, a second section and an third section defining the distal end, the second section being axially disposed between the first section and the third section, the first section being fixed in rotation with respect to the third section and the second section being movable in rotation with respect to the first section and to the third section to unlock the bayonet mechanism.

9. A syringe assembly according to claim 1, wherein the syringe body defines an inner chamber, the plunger rod being mounted to push a plunger in the inner chamber, the diameter of the plunger rod in the transversal direction being substantially 50% smaller than the diameter of the inner chamber.

* * * * *